United States Patent [19]

Loder

[11] Patent Number: 6,096,737

[45] Date of Patent: Aug. 1, 2000

[54] TREATMENT OF MULTIPLE SCLEROSIS (MS) AND OTHER DEMYELINATING CONDITIONS USING LOFEPRAMINE IN COMBINATION WITH L-PHENYLALANINE, TYROSINE OR TRYPTOPHAN AND POSSIBLY A VITAMIN B12 COMPOUND

[76] Inventor: Cari Loder, 127 Russell Court, Woburn Place, London WC1H 0LP, United Kingdom

[21] Appl. No.: 08/817,086

[22] PCT Filed: Oct. 5, 1995

[86] PCT No.: PCT/GB95/02361

§ 371 Date: Jun. 27, 1997

§ 102(e) Date: Jun. 27, 1997

[87] PCT Pub. No.: WO96/11009

PCT Pub. Date: Apr. 18, 1996

[30] Foreign Application Priority Data

Oct. 5, 1994 [GB] United Kingdom .................... 9420116
Apr. 26, 1995 [GB] United Kingdom .................... 9508482

[51] Int. Cl.[7] .......................... A61K 31/55; A61K 31/135
[52] U.S. Cl. ............................ 514/217; 514/213; 514/646
[58] Field of Search .................................... 514/210, 213, 514/217, 646

[56] References Cited

U.S. PATENT DOCUMENTS 4,409,243 10/1983 Lieb ........................................ 424/330
4,650,789 3/1987 Pollack ..................................... 514/23

FOREIGN PATENT DOCUMENTS 35 19 687 12/1986 Germany .
42 04 102 8/1993 Germany .
1 497 306 1/1978 United Kingdom .
2 082 910 3/1982 United Kingdom .
2 129 299 5/1984 United Kingdom .
WO 88/04173 6/1988 WIPO .

OTHER PUBLICATIONS

Abstract of Charles F. Scott, Jr., et al., "Experimental Allergic Encephalitis; Treatment with Drugs Which Alter CNS Serotonin Levels", *Journal of Immunopharmacology*, pp. 153–162, 1982.

D. Chadwick, et al., "5–Hydroxytryptophan–Induced Myoclonus in Guinea Pigs" *Journal of the Neurological Sciences*, pp. 157–165, 1976.

Karin N. Westlund, et al., "Serotonin is found in myelinated axons of the dorsolateral funiculus in monkeys" *Neuroscience Letters*, pp. 35–38, 1992.

E.H. Reynolds, "Multiple sclerosis and vitamin B12 metabolism", *Journal of Neuroimmunology*, pp. 225–230, 1992.

Guy M. Goodwin, "Tricyclic and newer antidepressants", *Handbook of Affective Disorders*, pp. 327–343, 1992.

Abdulla A.–B. Badawy, et al., "The Effects of Lofepramine and Desmethylimipramine on Tryptophan Metabolism and Disposition in the Rat", pp. 921–929, 1991.

Primary Examiner—Theodore J. Criares
Attorney, Agent, or Firm—Foley & Lardner

[57] ABSTRACT

The use of a combination of a tricyclic or tetracyclic antidepressant, a serotonin reuptake inhibitor, or a monoamine oxidase inhibitor with a neurotransmitter-inducing or precursor compound is proposed in the preparation of medication for the treatment or prevention of multiple sclerosis or other demyelinating conditions. For use in treatment to ameliorate the effects of a demyelinating condition, a daily regime is proposed of from 10 to 220 mg lofepramine and from 100 mg to 5 g of L-phenylalanine, optionally supplemented with injections of vitamin $B_{12}$.

14 Claims, No Drawings

TREATMENT OF MULTIPLE SCLEROSIS (MS) AND OTHER DEMYELINATING CONDITIONS USING LOFEPRAMINE IN COMBINATION WITH L-PHENYLALANINE, TYROSINE OR TRYPTOPHAN AND POSSIBLY A VITAMIN B12 COMPOUND

This invention relates to the treatment of Multiple Sclerosis (MS) and other Demyelinating Conditions.

Multiple sclerosis is a common and well known neurological disorder. It is characterised by episodic patches of inflammation and demyelination which can occur anywhere in the central nervous system (CNS) almost always without any involvement of the peripheral nerves. The occurrence of the patches is disseminated in time and space, hence the older alternative name of disseminated sclerosis. It is believed that the pathogenesis involves local disruption of the blood brain barrier, a local immune and inflammatory response, with consequent damage to myelin and hence to neurons.

Clinically, MS can present in both sexes and at any age. However, its most common presentation is in relatively young adults, often with a single focal lesion such as damage to the optic nerve (optic neuritis), an area of anaesthesia or paraesthesia or muscular weakness. Vertigo, nystagmus double vision, pain, incontinence, cerebellar signs, L'Hermitte's sign (paraesthesia or pain in the arms and legs on flexing the neck) and a large variety of less common symptoms may occur. The initial attack is often transient and it may be weeks, months or years before a further attack occurs. Some fortunate individuals may have a stable condition, while other unfortunate ones may have an unrelenting downhill course ending in complete paralysis. More commonly there is a long series of remissions and relapses, each relapse leaving the patient somewhat worse than before. Relapses may be triggered by stressful events or viral infections. Elevated body temperature almost invariably makes the condition worse whereas a reduced temperature, for example induced by a cold bath, may make the condition better.

There are no satisfactory treatments for MS. Steroids may produce a temporary improvement but any beneficial effect invariably wears off. Recent clinical trials have shown that interferon may somewhat reduce the risk of relapse. However, the effect is modest and most patients still deteriorate.

I have now developed a new and highly effective treatment for compensating for the effects of nerve damage caused by MS and other demyelinating conditions.

My invention is based on the use of a combination of an antidepressant or a monoamine oxidase inhibitor in combination with an inducer or precursor of a neurotransmitter. The two compounds may be administered in the same dosage form, or may be in separate dosage forms but a combined pack may be in separate packs for administration at separate times but so as to be effective together in the body.

Lofepramine and related tricyclic and tetracyclic antidepressants work by interfering with the inactivation of substances called neurotransmitters which are required for the normal transmission of nerve impulses from one nerve cell to the next. Such neurotransmitters, among them substances called noradrenaline and serotonin, are released from one nerve cell and activate the next one. They are inactivated by various mechanisms including rapidly being taken up into nerve cells and also enzymic destruction by enzymes known as monoamine oxidase inhibitors (MAOI). Lofepramine is a drug which inhibits neurotransmitter uptake and which is in the class of tricyclic antidepressants and which also has some MAOI activity. Newer drugs to treat depression are more active against serotonin and are known as selective serotonin reuptake inhibitors (SSRIs).

I have discovered that the use of L-phenylalanine (LPA), the precursor of noradrenaline, contributes to the therapeutic effect. In some individuals, however, an alternative may be L-tryptophan which is a precursor of the neurotransmitter, serotonin. Several different antidepressants including tricyclic antidepressants, SSRIs and MAOIs have beneficial effects but have consistently obtained the best results with lofepramine. Detailed information on lofepramine is given in the Merck Index. I have also noted that when the patient receives regular injections of vitamin $B_{12}$ the treatment works best.

As an example, a regime of 70 mg lofepramine and 500 mg LPA per day for over a year in my own case completely resolved severe unequivocally diagnosed MS. Over 100 other patients have done well on a similar regime, although some have been given other antidepressants either of the traditional tricyclic class, such as amitriptyline or imipramine, or the newer specialist serotonin uptake inhibitors or monoamine oxidase inhibitors. Four particular instances are given in the appendix. Most have done best on lofepramine. The doses of LPA have also varied from about 100 mg to up to 5 g per day, but best results are obtained with doses in the region of 500–2000 mg/day. The doses of antidepressants (with the proviso that minimum effective and maximum safe levels are determined according to the drug), lie broadly in the range 10 mg to 200 mg per day.

A background course of vitamin $B_{12}$ for example by injection, is also preferred and does have a beneficial effect. Daily amounts may for example be the conventional daily requirement for the vitamin.

Four case histories of patients other than myself illustrating the beneficial effects of my invention are given later herein. A total of 126 patients have now been tested and almost all have received benefit. This benefit has reached varying degrees with some only showing a small improvement and others a complete resolution of all symptoms such as I observed in myself.

TREATMENT EXAMPLES

A specific example of the use of the treatment is 70 mgs (half the therapeutic starting dose for depression) of lofepramine taken each morning with 500 mgs of L-phenylalanine, and 500 mgs of L-phenylalanine taken mid afternoon. For patients with the regular MS attacks of chronic progressive MS it is desirable to include an 8–10 week course of 1000 micrograms of hydroxocobalamin (intra muscular) per week at the start of treatment and then 1000 micrograms every ten days thereafter.

Other TCADs or MAOIs may be substituted for lofepramine and higher doses of antidepressants, L-phenylalanine may be indicated in individuals who fail to respond to the suggested levels. It is not advised to exceed the usual maximum prescribing dose of lofepramine (or another TCAD or MAOI) but doses between 70 mg and 210 mg of lofepramine can be prescribed. The doses of L-phenylalanine can then be increased in proportion to the dose of the TCAD or MAOI.

For instance: 70 mg lofepramine+500 mg L-phenylalanine twice per day.

120 mg lofepramine+1000 mg L-phenylalanine twice per day.

210 mg lofepramine+1500 mg L-phenylalanine twice per day.

This drug treatment is not appropriate for individuals with a history of cardiac problems, high blood pressure or for those suffering from PKU.

COMPOSITION EXAMPLES

1. Tablets of 500 mg L-tryptophan, or L-phenylalanine or the two combined to be taken at a dose of 1–10/day in accordance with an appropriate daily dose of an antidepressant chosen from the classes of tricycic or tetracyclic antidepressants, monoamine oxidase inhibitors or serotonin reuptake inhibitors. Examples of such drugs and some typical doses per day include lofepramine (70 mg), imipramine (100 mg), clomipramine (50 mg), amitriptyline (150 mg), nortriptyline (75 mg), mianserin, protriptyline (40 mg), venlafaxine, fluvoxamine (150 mg), fluoxetine (20 mg), maprotiline (75 mg), sertraline, pargyline, moclopemide, triazolopyridine, phenelzine (45 mg), tranylcypromine (20 mg), desipramine, dothiepin (70 mg), doxepin (100 mg), paroxetine, trimipramine, oxazine or viloxazine (500 mg). However, any other member of these classes of drugs not listed here may be used in this way, in doses indicated in standard texts.

2. Tablets as in (1) in which an appropriate dose of the amino acid is combined with an appropriate dose of the chosen antidepressant in the same dosage form so that an adequate daily dose of each can be provided.

3. Tablets containing 25–100 mg of lofepramine, together with 500 mg of phenylalanine, or 500 mg of tryptophan, or 250 mg of each. Normally such tablets would be used so as to provide a daily dose of 50–200 mg lofepramine together with 500–1000 mg of the amino acids.

4–6. Other appropriate dosage forms for 1–3 such as soft or hard gelatin capsules, emulsions, creams, whips, solutions, or any dosage form known to those skilled in the art.

CASE HISTORIES

Patient A 49y female. MS for 20 years. Symptoms on starting treatment: weak legs; rapid fatigue on exercise; bladder urgency and frequency with incontinence; arms too weak to allow self dressing; right hip pain. After 12 weeks treatment: complete disappearance of all symptoms.

Patient B 45y male. MS for 12 years. Symptoms on starting treatment: confined to wheelchair; legs spastic and weak; arms weak and rapidly fatigued; hands numb; bladder urgency and incontinence. After 8 weeks treatment: fatigue and weakness of arms and legs greatly improved; spasticity less; bladder improved; walking on crutches instead of wheelchair.

Patient C 38y male. MS for 2 years. Symptoms on starting treatment: badly slurred speech; fatigue; bladder urgency and frequency; limited to half a mile walking even with a stick; poor hand control and writing. After 6 weeks treatment: fatigue better; speech much less slurred; eyesight and writing improved; can walk half a mile without a stick.

Patient D 40y female. MS for 3 years. Symptoms on starting treatment: poor balance; optic neuritis; spasticity and spasms with pain in legs and feet; bladder urgency; "shimmering" sight. After 3 weeks treatment: spasms, spasticity and pain completely relieved; bladder function better; balance better; "shimmering" sensation disappeared.

What is claimed is:

1. A method of treating or preventing nerve damage caused by multiple sclerosis, comprising administering to a patient in need thereof a combination of lofepramine, in an amount ranging from 10 mg to 220 mg per day and L-phenylalanine, in an amount of from about 100 mg to 5 g per day.

2. A method according to claim 1, comprising administering a vitamin $B_{12}$ compound.

3. A method according to claim 2, wherein said vitamin $B_{12}$ compound is cyanocobalamin or hydroxocobalamin.

4. A method according to claim 1, wherein the lofepramine and L-phenylalanine are administered together daily, followed by a further daily dose L-phenylalanine.

5. A method according to claim 1, wherein lofepramine is administered in an amount of from 10 mg to 200 mg per day.

6. A method according to claim 5, wherein L-phenylalanine is administered in an amount of from 500 mg to 2000 mg per day.

7. A method of treating or preventing multiple sclerosis, comprising co-administering to a patient in need thereof lofepramine, in an amount ranging from 10 mg to 220 mg per day and L-phenylalanine, in an amount of from about 100 mg to 5 g per day.

8. A method according to claim 7, comprising administering a vitamin $B_{12}$ compound.

9. A method according to claim 7, wherein lofepramine is administered in an amount of from 10 mg to 200 mg per day.

10. A method according to claim 9, wherein L-phenylalanine is administered in an amount of from 500 mg to 2000 mg per day.

11. A package, comprising a unit dose of from 10–220 mg lofepramine and a unit dose of from 100 mg to 5 g of L-phenylalanine.

12. A package according to claim 11, comprising a unit dose of from 70–210 mg lofepramine and a unit dose of from 500 mg to 3000 mg of L-phenylalanine.

13. A package according to claim 11, comprising a vitamin $B_{12}$ compound.

14. A composition, comprising a unit dosage form of 25–100 mg lofepramine and 400–600 mg L-phenylalanine.

* * * * *